United States Patent
Zuidema et al.

(10) Patent No.: US 10,710,060 B2
(45) Date of Patent: Jul. 14, 2020

(54) CATALYST COMPOSITION COMPRISING CON-TYPE ZEOLITE AND ZSM-5-TYPE ZEOLITE, PREPARATION AND PROCESS USING SUCH COMPOSITION

(71) Applicant: SHELL OIL COMPANY, Houston, TX (US)

(72) Inventors: Erik Zuidema, Amsterdam (NL); Dirk Willem Zant, Amsterdam (NL)

(73) Assignee: Shell Oil Company, Houston, TX (US)

( * ) Notice: Subject to any disclaimer, the term of this patent is extended or adjusted under 35 U.S.C. 154(b) by 69 days.

(21) Appl. No.: 16/316,749

(22) PCT Filed: Jul. 10, 2017

(86) PCT No.: PCT/EP2017/067222
§ 371 (c)(1),
(2) Date: Jan. 10, 2019

(87) PCT Pub. No.: WO2018/011122
PCT Pub. Date: Jan. 18, 2018

(65) Prior Publication Data
US 2019/0299197 A1    Oct. 3, 2019

Related U.S. Application Data

(60) Provisional application No. 62/361,767, filed on Jul. 13, 2016.

(51) Int. Cl.

| B01J 29/80 | (2006.01) |
|---|---|
| B01J 29/48 | (2006.01) |
| B01J 29/78 | (2006.01) |
| B01J 35/02 | (2006.01) |
| B01J 37/00 | (2006.01) |
| B01J 37/02 | (2006.01) |
| B01J 37/08 | (2006.01) |
| C07C 6/12 | (2006.01) |
| B01J 37/18 | (2006.01) |
| B01J 35/10 | (2006.01) |
| B01J 29/72 | (2006.01) |

(52) U.S. Cl.
CPC ........... B01J 29/80 (2013.01); B01J 29/48 (2013.01); B01J 29/78 (2013.01); B01J 35/023 (2013.01); B01J 35/1019 (2013.01); B01J 37/0018 (2013.01); B01J 37/0201 (2013.01); B01J 37/08 (2013.01); B01J 37/18 (2013.01); C07C 6/126 (2013.01); B01J 29/72 (2013.01); B01J 2229/20 (2013.01); B01J 2229/42 (2013.01); C07C 2529/48 (2013.01); C07C 2529/78 (2013.01); C07C 2529/80 (2013.01); Y02P 20/52 (2015.11)

(58) Field of Classification Search
None
See application file for complete search history.

(56) References Cited

U.S. PATENT DOCUMENTS

| 3,702,886 | A | 11/1972 | Argauer et al. |
|---|---|---|---|
| 4,467,129 | A | 8/1984 | Iwayama et al. |
| 4,511,547 | A | 4/1985 | Iwayama et al. |
| 4,910,006 | A | 3/1990 | Zones et al. |
| 4,963,337 | A | 10/1990 | Zones |
| 5,952,536 | A | 9/1999 | Nacamuli et al. |
| 7,648,694 | B2 | 1/2010 | Burton, Jr. |
| 2010/0029467 | A1 | 2/2010 | Inui |
| 2011/0172478 | A1 | 7/2011 | Ma et al. |
| 2013/0157841 | A1* | 6/2013 | Lacheen ............... C10G 2/332 502/74 |
| 2013/0158138 | A1* | 6/2013 | Jothimurugesan ..... B01J 29/045 518/715 |
| 2015/0166913 | A1* | 6/2015 | Brody ...................... B01J 29/70 48/127.7 |
| 2016/0102590 | A1* | 4/2016 | Weiss .................... F01N 3/0814 423/245.1 |
| 2016/0228818 | A1* | 8/2016 | Chang ..................... F01N 3/035 |
| 2016/0367973 | A1* | 12/2016 | Larsson ............... B01J 35/0006 |
| 2016/0367974 | A1* | 12/2016 | Larsson .................. B01J 23/44 |
| 2017/0137720 | A1* | 5/2017 | Harandi ................... B01J 29/80 |
| 2018/0311651 | A1* | 11/2018 | Ravon .................. B01J 37/0201 |
| 2019/0060833 | A1* | 2/2019 | Hoke ..................... F01N 3/103 |

FOREIGN PATENT DOCUMENTS

| EP | 0307113 A1 | 3/1989 |
|---|---|---|
| EP | 0792251 B1 | 4/2001 |
| EP | 2022564 A1 | 2/2009 |
| EP | 1727878 B1 | 4/2011 |

OTHER PUBLICATIONS

International Search Report and Written Opinion received for PCT Patent Application No. PCT/EP2017/067222, dated Sep. 25, 2017, 11 pages.
Baerlocher et al., Atlas of Zeolite Framework Types, Sixth Revised Edition, 2007, 6 pages.

* cited by examiner

*Primary Examiner* — Ali Z Fadhel
(74) *Attorney, Agent, or Firm* — Charles W. Stewart

(57) ABSTRACT

The invention relates to a catalyst composition comprising a) a carrier comprising: (i) of from 5 to 95 wt % of CON type zeolite, (ii) of from 5 to 95 wt % of ZSM-5 type zeolite; and (iii) of from 10 to 60 wt % of inorganic binder; and b) of from 0.001 to 10 wt % one or more metals selected from the group consisting of Group 6-11 of the IUPAC Periodic Table of Elements. The invention further relates to a process for preparing the catalyst composition and to a process for the conversion of an alkylaromatic hydrocarbons containing feedstock using a catalyst prepared by the present process.

10 Claims, No Drawings

CATALYST COMPOSITION COMPRISING CON-TYPE ZEOLITE AND ZSM-5-TYPE ZEOLITE, PREPARATION AND PROCESS USING SUCH COMPOSITION

CROSS REFERENCE TO RELATED APPLICATIONS

This is a national stage application of International Application No. PCT/EP2017/067222, filed 10 Jul. 2017, which claims benefit of priority to U.S. Patent Application No. 62/361,767, filed 13 Jul. 2016.

CROSS-REFERENCE TO RELATED APPLICATION

The present application claims priority to U.S. Provisional Application No. 62/361,767, filed 13 Jul. 2016, the disclosure of which is herein incorporated by reference.

FIELD OF THE INVENTION

The present invention relates to a process for preparing a catalyst and a process for the conversion of an aromatic hydrocarbons containing feedstock using the catalyst.

BACKGROUND OF THE INVENTION

Reformate is an aromatic product obtained by the catalyzed conversion of straight-run hydrocarbons boiling in the 70 to 190° C. range, such as straight-run naphtha. The reformate feedstock itself is obtained by fractionation or distillation of crude petroleum oil, its composition varying depending on the source of the crude oil, but generally having a low aromatics content. On conversion to reformate, the aromatics content is considerably increased and the resulting hydrocarbon mixture becomes highly desirable as a source of valuable chemical intermediates and as a component for gasoline. The principle components are a group of aromatics often referred to as BTX: benzene, toluene and the xylenes, including ethylbenzene. Other components may be present such as their hydrogenated homologues, e.g. cyclohexane.

Of the BTX group the most valuable components are benzene and the xylenes, and therefore BTX is often subjected to processing to increase the proportion of those two aromatics: hydrodealkylation of toluene to benzene and toluene disproportionation to benzene and xylenes. Within the xylenes, para-xylene is the most useful commodity. Xylene isomerisation or transalkylation processes have been developed to increase the proportion of para-xylene.

A further process that the gasoline producer can utilize is the hydrodealkylation of ethylbenzene to benzene.

Generally, the gasoline producer will isolate a fraction containing aromatic compounds containing at least 8 carbon atoms from the reformate stream, and then subject this stream to xylene isomerisation with the aim of maximising the para-xylene component. Xylene isomerisation is a catalytic process. Normally the para-xylene is then separated out to leave benzene, toluene (unless toluene conversion processes have already been applied), remaining mixed xylenes including ethylbenzene and aromatic compounds containing at least 9 carbon atoms. This alkylaromatic stream can be can be converted by (i) dealkylation to selectively eliminate ethylbenzene and to increase the yield of benzene while isomerizing xylenes to equilibrium or (ii) further reforming to convert ethylbenzene to xylenes while isomerizing xylenes to equilibrium or (iii) transalkylation by isomerizing xylenes to equilibrium and dealkylating specific alkylaromatic compounds. The latter process is the subject of the present invention.

U.S. Pat. No. 5,952,536 describes gas phase aromatics transalkylation with the help of a catalyst comprising a zeolite selected from the group consisting of SSZ-26, Al-SSZ-33, CIT-1, SSZ-35 and SSZ-44.

In transalkylation at this latter stage of the alkylaromatic treatment, it is advantageous if the catalyst is active in converting specific alkylaromatic compounds more especially methylethylbenzene, more preferably at relatively high xylene yield and/or relatively high total conversion. Furthermore, it is advantageous if the catalyst gives a product having a low ratio of ethylbenzene to total aromatic compounds having 8 carbon atoms. Furthermore, it is advantageous if the transalkylation catalyst is active, produces product which is high in xylene content, produces benzene of high purity, produces xylene of high purity, limits aromatics loss and/or isomerizes xylene to equilibrium. Aromatics may typically be lost by addition of hydrogen to form, for example, alkenes or alkanes.

Object of the present invention is to provide a catalyst which can be used in such process, a process in which such catalyst is used and a process for preparing such catalyst.

SUMMARY OF THE INVENTION

The present invention relates to a catalyst composition comprising (a) a carrier comprising (i) CON type zeolite in an amount in the range of from 5 to 95% by weight (wt %), based on total weight of carrier, (ii) ZSM-5 type zeolite in an amount of from 5 to 95 wt %, based on total weight of carrier; and (iii) an inorganic binder in an amount in the range of from 10 to 60 wt %, based on total weight of carrier; and (b) of from 0.001 to 10 wt % one or more metals selected from the group consisting of Group 6-11 of the IUPAC Periodic Table of Elements.

The present invention further relates to a process for preparing such catalyst composition, comprising the steps of (a) mixing the CON type zeolite, ZSM-5 type zeolite and inorganic binder and extruding the mixture obtained, (b) optionally subjecting the extrudates obtained in step (a) to a heat treatment, (c) impregnating the calcined extrudates with a solution comprising one or more metals selected from the group consisting of Group 6-11 of the IUPAC Periodic Table of Elements, and (d) optionally subjecting the impregnated extrudates obtained in step (c) to a heat treatment.

The present invention further relates to a process for the conversion of a feedstock containing alkylaromatic hydrocarbons using a catalyst of the invention or prepared by a catalyst preparation process of the invention.

DETAILED DESCRIPTION OF THE INVENTION

CON type zeolite is well known in the art. For the present application, the CON zeolite is as defined and described in "Atlas of Zeolite Framework Types," Baerlocher et al., Sixth Rev. Ed. (Elsevier 2007). Preferred CON type zeolites for use in the present invention are SSZ-26 and SSZ-33. Most preferred is zeolite SSZ-26. Zeolite SSZ-26 can be prepared as described in U.S. Pat. No. 4,910,006. Zeolite SSZ-33 can be prepared as described in U.S. Pat. No. 4,963,337. As synthesized, zeolite SSZ-33 tends to be a borosilicate. The boron can be substituted by other elements to produce active transalkylation catalysts.

ZSM-5 zeolite also is as defined and described in "Atlas of Zeolite Framework Types," Baerlocher et al., Sixth Rev. Ed. (Elsevier 2007).

The catalyst composition of the present invention comprises a carrier which preferably comprises CON type zeolite in an amount of from 20 to 90 wt %, based on total weight of carrier. Preferably, the CON type zeolite is present in an amount in the range of from 30 to 70 wt %, more preferably in the range of from 40 to 60 wt %, based on total weight of carrier. The CON type zeolite preferably has a silica to alumina molar ratio in the range of from 10 to 120, preferably in the range of 40 to 110, and more preferably in the range of from 50 to 100.

The present catalyst composition comprises a carrier which preferably comprises a ZSM-5 type zeolite in an amount of 10 to 70 wt %, based on total weight of carrier material compound. Preferably, the ZSM-5 type zeolite is present in an amount in the range of from 15 to 60 wt %, more preferably in the range of from 20 to 40 wt %, based on total weight of carrier. The present catalyst composition preferably has a higher content of CON zeolite than of ZSM-5 type zeolite. More preferably, the CON zeolite content of the present catalyst composition preferably is at least 5 wt %, and more preferably at least 10 wt % higher than the ZSM-5 content.

The ZSM-5 type zeolite preferably has a silica to alumina molar ratio in the range of from 10 to 50, preferably in the range of 15 to 40, and more preferably in the range of from 18 to 35.

The ZSM-5 type zeolite preferably has a number average particle size in the range of 20 to 500 nm. Preferably, the ZSM-5 type zeolite has a number average particle size in the range of from 30 to 300 nm, more preferably in the range of from 50 to 200 nm. It was observed that the small average particle of the ZSM-5 type zeolite used in accordance with the present invention can improve the benzene purity.

Suitable ZSM-5 type zeolites to be used in accordance with the present invention can be prepared as for example described in U.S. Pat. Nos. 3,702,886 and 4,511,547. Suitable examples of ZSM-5 type zeolites include CBV 3014E, CBV 3020E and CBV 8014, available commercially from Zeolyst International.

The catalyst of the present invention preferably contains an inorganic binder in an amount in the range of from 10 to 50 wt %, based on total weight of carrier. Preferably, the inorganic binder is present in an amount in the range of from 10 to 40 wt %, more preferably in the range of from 15 to 30 wt %, based on total carrier.

Suitably, the inorganic binder is selected from the group consisting of gamma-alumina, silica, silica-alumina, bentonite, kaolin, titania, zirconia, ceria, gallia, climotilolite, montmorillonite, and any mixture thereof. Preferred inorganic binder is alumina, more specifically gamma alumina.

In shaped form, for example as extrudates, the carrier generally has a BET surface area falling in the range of from 200 to 600 m²/g, preferably 250 to 500 m²/g, more preferably from 350 to 450 m²/g. The surface area suitably is measured according to ASTM D3663-03(2015). Furthermore, the extrudates preferably have a pore volume, by mercury intrusion, in the range of from 0.2 to 1.2 ml/g, preferably 0.4 to 1.0 ml/g, more preferably 0.5 to 0.8 ml/g.

The present catalyst composition may be shaped in any particular form. Suitable shapes include trilobes and cylinders, Preferably, the present catalyst composition is in the shape of trilobes.

The carrier preferably consists of CON type zeolite, ZSM-5 type zeolite and alumina.

The carrier can be prepared by shaping the carrier and subsequently subjecting the carrier to a heat treatment. The heat treatment preferably comprises calcining the shaped carrier optionally preceded by drying. Drying temperatures can suitably be in the range of from 50 to 200° C. Drying times can suitably be in the range of from 0.5 to 24 hours. Calcination temperatures can suitably be in the range of from 200 to 800° C., preferably in the range of from 300 to 600° C. In the calcination of the carrier material, a relatively short time can suitably be applied such as in the range of from 0.5 to 5 hours. The calcination can suitably be carried out at a temperature in the range of from 400 to 700° C., preferably in the range of from 450 to 600° C.

The present catalyst composition comprises one or more metals chosen from the group consisting of Groups 6-11 of the IUPAC Periodic Table of Elements dated 1 May 2013. Preferably, the catalyst composition comprises one or more metals chosen from the group consisting of tungsten, vanadium, molybdenum, rhenium, nickel, cobalt, chromium, manganese, platinum and palladium. Most preferably, the metal is molybdenum.

The amount of metal preferably is in the range of from 0.001 to 10 wt %, as metal based on total weight of catalyst, more preferably in the range of from 0.1 to 10 wt %, more preferably in the range of from 2 to 9 wt %, more preferably of from 2 to 8 wt %, more preferably of from 2 to 6 wt % of metal based on total weight of catalyst. The metals can be incorporated in the carrier with the help of a metal salt solution. Preferably, the metals are incorporated by pore volume impregnation.

The amount of metal is calculated as metal independent from the actual compound present.

The catalyst composition of the invention can suitably have such shape that a reactor filled with the catalyst particles has an average void fraction of at least 10% by volume, preferably in the range of from 20 to 70%, more preferably in the range of from 35 to 55% by volume.

After incorporating the metal in the carrier, the impregnated carrier preferably is subjected to a heat treatment. This heat treatment preferably is of from 100 to at most 500° C., preferably of from 200 to at most 450° C.

Before use of the catalyst composition, it will be preferred that the metals on the catalyst composition are in metallic (and not oxidic) form. Accordingly, the catalyst composition preferably is subjected to reducing conditions, which are, for example, heating in a reducing atmosphere, such as in hydrogen optionally diluted by an inert gas, such as nitrogen or carbon dioxide, at temperature in the range of from 150 to 600° C. for a period of time in the range from 0.5 to 5 hours.

The present catalyst preferably is used in a process for conversion, more specifically transalkylation, of a feedstock containing alkylaromatic hydrocarbons.

Suitably, the alkylaromatic hydrocarbon feedstock comprises at least 70 wt % of toluene and alkylaromatics containing at least 9 carbon atoms, more specifically at least 80 wt %, more specifically at least 90 wt %. Further compounds which can be present are ethylbenzene and ethyl-xylene. Preferably, the feedstock comprises toluene and alkylaromatic compounds containing at least 9 carbon atoms in a weight ratio of from 10:90 to 90:10. Most preferably, the alkylaromatic hydrocarbon feedstock comprises of from 35 to 75 wt % of toluene and of from 25 to 65 wt % of alkylaromatic compounds containing at least 9 carbon atoms.

The feedstock suitably is contacted with the catalyst composition in the presence of hydrogen. This may be carried out in a fixed bed system, a moving bed system, or a fluidized bed system. Such systems may be operated continuously or in batch fashion. Preference is given to continuous operation in a fixed bed system. The catalyst may be used in one reactor or in several separate reactors in series or operated in a swing system to ensure continuous operation during catalyst change-out.

The present transalkylation process preferably is carried out at a temperature in the range of from 200 to 600° C., preferably in the range of from 250 to 500° C., and more preferably in the range of from 300 to 400 C°.

The process preferably is carried out at a pressure in the range of from 1 to 30 barg, preferably at a pressure in the range of from 2 to 20 barg, and more preferably at a pressure in the range of from 2 to 10 barg.

The weight space velocity applied in the process is suitably in the range of from 0.2 to 30 hr$^{-1}$, preferably from 2 to 20 hr$^{-1}$, and more preferably in the range of from 3 to 6 hr$^{-1}$.

The feed to hydrogen ratio mol·mol$^{-1}$ is in the range of from 0.5 to 100, preferably in the range of from 1 to 10.

The reaction effluent preferably will be recovered and subjected to a distillation treatment to remove the desired products, more specifically xylene and benzene. Unreacted reactant such as for instance toluene can suitably be recycled for further reaction.

The present invention will now be illustrated by the following Examples.

analysis. A total pressure of 30 barg and a hydrogen:hydrocarbon molar ratio of 5 were maintained throughout the experiment. Prior to the test, catalysts were dried in a flow of hydrogen at room temperature and atmospheric pressure for 1 hour, then heated to 400° C. for 1 hour, pressurized to 30 barg, maintained under these conditions for a further 1 hour, and finally cooled to 310° C. The hydrocarbon feed was introduced at a WHSV of 4 h$^{-1}$, and the systems were operated for 24 hours to stabilize the performance. The key performance parameters at this temperature after 24 hours are compared in Table 1.

TABLE 1

| Feed composition | |
| --- | --- |
| Component | Content (wt %) |
| Toluene | 50.4 |
| Trimethylbenzenes (TMB) | 28.6 |
| Methylethylbenzene (MEB) | 11.0 |
| Propylbenzenes | 0.8 |
| Indane | 1.4 |
| Ethyl-xylenes | 7.0 |
| Tetramethylbenzenes | 0.5 |
| C10+ rest | 0.3 |

TABLE 2

Catalyst overview and performances in transalkylation

| Type | wt % | (wt %) | wt % | Total conversion wt % | Xylene yield wt % | MEB conversion (%) | Ethylbenzene/ aromatics containing 8 carbons (%) |
| --- | --- | --- | --- | --- | --- | --- | --- |
| CON | 80 | ZSM5 | 0 | 44.8 | 32.3 | 48.4 | 7.6 |
| CON | 72 | ZSM5 | 8 | 45.5 | 32.8 | 54.6 | 6.8 |
| CON | 64 | ZSM5 | 16 | 45.5 | 32.8 | 58.4 | 6.2 |
| CON | 56 | ZSM5 | 24 | 45.7 | 32.9 | 62.7 | 5.4 |
| CON | 48 | ZSM5 | 32 | 44.9 | 32.1 | 67.3 | 4.8 |
| CON | 40 | ZSM5 | 40 | 43.7 | 31.4 | 69.6 | 4.2 |

EXAMPLES

Example 1

ZSM-5 zeolite having a silica to alumina molar ratio of 23 and a number average crystal size of 100 nm was obtained from Zeolyst International. CON zeolite with a silica to alumina molar ratio of 79 was prepared according to the process as described in U.S. Pat. No. 7,648,694.

Carrier was prepared by extruding mixtures of 80 wt % of zeolite and 20 wt % of alumina (Pural SB1 commercially available from Sasol). The extrudates obtained were dried and calcined at about 550° C. for 1 hour. 0.3 wt % Rhenium was incorporated into the calcined extrudates by pore-volume impregnation using a solution of perrhenic acid. The impregnated extrudates were dried for two hours at 140° C., and then calcined for 1 hour at 480° C. The resulting catalyst composition was ground to 30-80 mesh particles, and mixed in different ratios to obtain various transalkylation catalyst systems as described in Table 2.

Catalyst systems were evaluated in a pilot plant for the transalkylation of a typical transalkylation feed with a composition summarized in Table 1, using on-line GC Table 2 shows that the present catalyst composition results in higher MEB conversion in transalkylation than catalyst solely containing CON zeolite while both the xylene yield and/total conversion are relatively high. Furthermore, the present catalyst composition results in product having a low ratio of ethylbenzene to total aromatic compounds having 8 carbon atoms at relatively high xylene yield and/relatively high total conversion.

That which is claimed is:

1. A catalyst composition comprising:
   (a) a carrier comprising (i) CON zeolite in an amount in the range of from 5 to 85 wt %, based on total weight of carrier, (ii) ZSM-5 zeolite in an amount of from 5 to 85 wt %, based on total weight of carrier; and (iii) an inorganic binder in an amount in the range of from 10 to 60 wt %, based on total weight of carrier; and
   (b) of from 0.001 to 10 wt % one or more metals selected from the group consisting of Groups 6-11 of the IUPAC Periodic Table of Elements.

2. The catalyst composition according to claim 1 in which the carrier comprises CON zeolite in an amount in the range of from 20 to 85 wt %, based on total weight of carrier.

3. The catalyst composition according to claim 1 in which the carrier comprises ZSM-5 zeolite in an amount of from 10 to 70 wt %, based on total weight of carrier.

4. The catalyst composition according to claim 1 in which the one or more metals comprise molybdenum in an amount in the range of from 1 to 10 wt %, as metal based on total weight of catalyst.

5. The catalyst composition according to claim 1, wherein the ZSM-5 zeolite has a silica to alumina molar ratio in the range of from 15 to 35.

6. The catalyst composition according to claim 1, wherein the ZSM-5 zeolite has a number average crystal size in the range of from 50 to 200 nm.

7. A process for preparing the catalyst composition according to claim 1, comprising the steps of:
(a) mixing the CON zeolite, the ZSM-5 zeolite and the inorganic binder to produce a mixture and extruding the mixture to produce extrudates,
(b) optionally subjecting the extrudates obtained in step (a) to a heat treatment to produce calcined extrudate,
(c) impregnating the extrudates or the calcined extrudates with a solution comprising one or more metals selected from the group consisting of Group 6-11 of the IUPAC Periodic Table of Elements, and
(d) optionally subjecting the impregnated extrudates obtained in step (c) to a heat treatment.

8. A process for the conversion of a feedstock containing alkylaromatic hydrocarbons said process comprising contacting the feedstock with the catalyst of claim 1.

9. The process according to claim 8 wherein the feedstock comprises toluene and alkylaromatic compounds containing at least 9 carbon atoms in a weight ratio of from 10:90 to 90:10.

10. The process according to claim 8, wherein the feedstock comprises of from 35 to 75 wt % of toluene and of from 25 to 65 wt % of alkylaromatic compounds containing at least 9 carbon atoms.

* * * * *